United States Patent [19]

Bittmann et al.

[11] Patent Number: 4,932,964
[45] Date of Patent: Jun. 12, 1990

[54] ARTIFICIAL BODY FOR A PROSTHESIS

[75] Inventors: Peter Bittmann, Herrliberg; Peter Dittes, Oberdurnten; Werner Muller, Wiesendangen, all of Switzerland

[73] Assignees: Sulzer Brothers Limited, Winterthur; IMS-Biopur AG, Freienbach, both of Switzerland

[21] Appl. No.: 278,806

[22] Filed: Dec. 1, 1988

[30] Foreign Application Priority Data

Dec. 7, 1987 [CH] Switzerland .................. 4769/87

[51] Int. Cl.$^5$ ................................ A61F 2/06
[52] U.S. Cl. ............................ 623/1; 623/12; 623/66
[58] Field of Search ............ 623/1, 12, 66; 600/36; 264/41

[56] References Cited

U.S. PATENT DOCUMENTS

| 4,355,426 | 10/1982 | MacGregor | 3/1.4 |
| 4,384,023 | 5/1983 | Okamura et al. | 264/41 |
| 4,647,416 | 3/1987 | Seiler, Jr. et al. | 623/1 |
| 4,804,381 | 2/1989 | Turina et al. | 623/1 |
| 4,804,382 | 2/1989 | Turina et al. | 623/1 |
| 4,813,966 | 3/1989 | Gilding et al. | 623/1 X |
| 4,822,352 | 4/1989 | Joh et al. | 623/1 |
| 4,834,746 | 5/1989 | Kira | 623/1 |

FOREIGN PATENT DOCUMENTS

| 0130401 | 1/1985 | European Pat. Off. |
| 0216149 | 4/1987 | European Pat. Off. |
| 0248246 | 12/1987 | European Pat. Off. |
| 0248247 | 12/1987 | European Pat. Off. |
| 0064370 | 3/1987 | Japan | 623/12 |

Primary Examiner—Randall L. Green
Assistant Examiner—N. Paul
Attorney, Agent, or Firm—Kenyon & Kenyon

[57] ABSTRACT

A prosthesis wall for an artificial organ, e.g. an artificial arterial blood vessel, to be coated without gaps on one side with biologically active epithelial, e.g. endothelial cells is provided with a structure of open continuous micropores a few microns in size. The pore size is limited to between 0.1 and 3 microns, at least on the surface to be coated with cells with the thickness of the partitions between the pores being not more than 3 microns to permit a continuous layer of endothelial cells with prolonged and firm adhesion to the prosthesis to be subsequently formed.

11 Claims, 1 Drawing Sheet

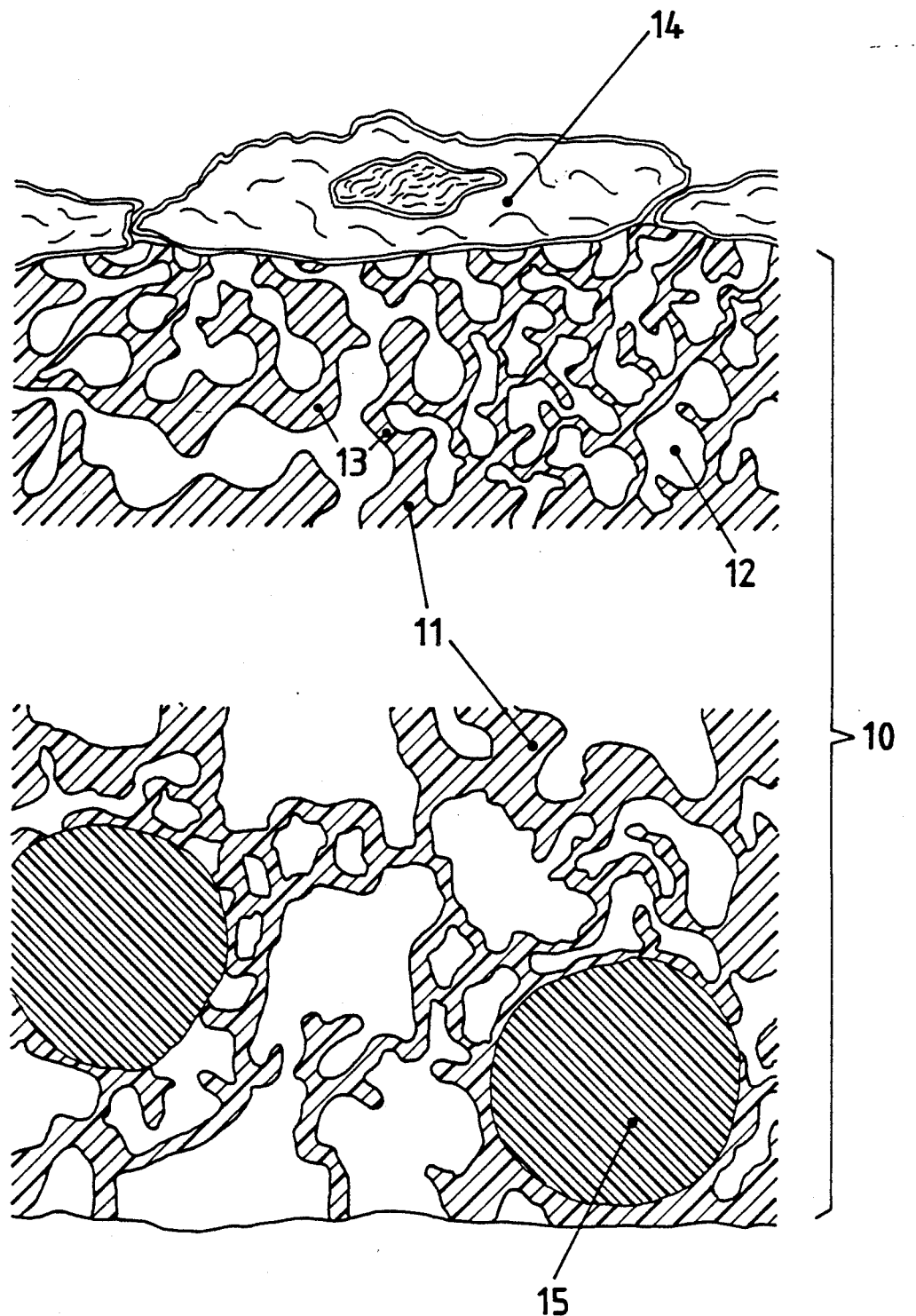

ARTIFICIAL BODY FOR A PROSTHESIS

This invention relates to an artificial body for a prosthesis. More particularly, this invention relates to an artificial organ or vessel wall of a bio-inert membrane-like prosthesis.

Heretofore, various types of constructions have been known for replacing small lumen arterial blood vessels, for example, having diameters smaller than 7 millimeters. For example, such constructions have been described in U.S. Pat. No. 4,355,426, published European Patent Application No. 0130401 and WO 85/03444 and WO 85/03445. Generally, the prosthesis described in these publications are made of polymerized elastomers, such as polyurethane. Further, in order to meet physiological requirements, the prosthesis have been internally lined with a continuous layer of epithelial, e.g. endothelial cells. The prosthesis wall, therefore, has had open intercommunicating micropores which may, if required, increase in size towards the exterior and can extend through the entire wall thickness, which may be several millimeters (mm). Further, the innermost layers of the vessel walls facing the endothelial cells have had pores about 0.5 to 20 microns ($\mu$m) in size.

In practice, the existing constructions have various disadvantages, particularly if the prosthesis wall coated with endothelial cells is exposed to shear forces from a blood stream flowing past. One disadvantage, for example, is that epithelial cells do not form a continuous layer growing over structures having pores larger than 3 microns since they grow into larger pores and form a circular lining on them like capillaries, instead of producing a continuous surface layer. Further, it has been found that smooth surfaces with more than a 3 micron width or length between the pores gives very bad adhesion.

Accordingly, it is an object of the invention to improve existing constructions of microporous walls for artificial organs or vessels.

It is another object of the invention to provide an improved construction for use as an artificial arterial blood vessel.

It is another object of the invention to be able to provide a continuous layer of viable epithelial cells on a microporous wall of an artificial membrane.

It is another object of the invention to improve the long-term adhesion of living cells on the wall of a prosthesis.

Briefly, the invention is directed to an artificial body of bio-inert membrane-like plastic material which has a wall defining a surface. In accordance with the invention, the wall is provided with a plurality of continuous open micropores at least partly communicating with each other and which are of a maximum linear dimension between 0.1 and 3 microns as well as a plurality of partitions between the micropores which have a maximum width at the surface of not more than 3 microns. With this construction, a continuous layer of epithelial cells can be coated on the surface of the body.

The microporous structure thus has very fine pores upon which a continuous layer of epithelial cells may be formed. On the one hand, pores not exceeding the above-noted very fine dimensions are not "regarded" by epithelial cells as capillary tubes into which the cells may grow in rings. Thus, the cells form a continuous layer covering these pores. On the other hand, the very fine pores form a cross-linked network on a perforated rough surface, into which fibrillar components of the sub-epithelial extracellular matrix (ECM) grow, starting from the basal cell membrane or the basal lamina, and form "bunched fibers" which are mechanically anchored to the substrate.

The fibrillar elements can be adequately nourished and renewed only if a minimum pore size of 0.1 micron is ensured.

It has been found advantageous if the depth of the very fine-pore region on the surface of the wall is between 0.5 and 3 microns. The mechanical anchoring of the fibrillar elements can be improved if the very fine pores communicate with one another at least partly inside the depth range.

The vessel wall can be made of elastomers, such as styrene-butadiene-styrene block polymers and mixtures thereof with e.g. polyurethanes (PUR) or with PUR-polysiloxane copolymers, natural or synthetic rubber or other materials with elastomeric properties. The elastomers are used in the form of 1–70% solutions. Solvents for the elastomers can be aliphatic, aromatic, polar or non-polar compounds, such as xylene, decahydronaphthalene, N,N-dimethyl acetamide, dimethyl formamide, N-methyl pyrrolidone, ketones, aldehydes, alcohols or mixtures thereof.

A tubular porous prosthesis wall having pores which can increase in size in known manner towards the exterior, may be manufactured by known dipping or extrusion processes. In this case, the pore structure is obtained by a conventional phase separation process for coagulating an elastomer. The pore size can be influenced via the temperature maintained during phase separation, the concentration of elastomers and the composition of the solvent for immersion treatment and phase separation.

The separating medium can be a polar or non-polar, organic or inorganic detergent such as $H_2O$, alcohols, aldehydes, sulphonates, ethoxylates or propoxylates, cyclic or heterocyclic hydrocarbon compounds, amines, acids, or mixture of the various compounds.

It is also, of course, possible in order to obtain a compliance similar to a natural vessel, to incorporate a reinforcing material in the prosthesis wall in known manner, outside the depth of the very fine pores. The reinforcing material can be made of organic or inorganic substances in the form of a mat, knitted or woven structure or as a shaped monofilament. The materials can be textured or flat.

The pore sizes and wall thicknesses can be inspected and measured in a scanning electron microscope.

EXAMPLE

A number of layers of a polyurethane-ether compound cross-linked with urea were produced on a rod of chromium-nickel-vanadium-steel alloy a few millimeters in diameter by the known dipping method, by immersion in a 10% N-methylpyrrodlidone solution. Between the individual immersion steps, the phases were separated by a 1% (per mille) solution of nonyl phenol ethoxylate in water.

After the second separation step, a polyester mat was incorporated into the prosthesis to reinforce the wall. Coating was then continued until the wall reached the desired thickness, e.g. between 0.1 and 1 millimeters.

Finally, the prosthesis was released from the matrix, purified from any remaining solvents by drying and extraction, and sterilized.

The invention thus provides a construction which can be used as the wall of an artificial organ or as the wall of a vessel such as arterial blood vessel. In any case, the wall is such that a continuous layer of epithelial cells can be coated thereon without interruptions caused, for example, by pores larger than 3 microns. Further, by limiting the width of the partitions between the pores, the adhesion of the cells to the wall is improved. In the case where the prosthesis wall is exposed to a flowing blood stream, the shear forces of the blood stream can be better resisted.

The drawing illustrates an artifical body 10 of bioinert membrane-like plastic material which has a wall 11 defining a surface in which a plurality of continuous open micro-pores 12 are disposed with intervening partitions 13. The pores 12 have a maximum linear dimension between 0.1 and 3 microns while the partitions have a maximum width of not more than 3 microns. As indicated, a continuous layer 14 of epithelial cells can be coated on the surface of the wall 11. In addition, a reinforcing material 15 may be disposed in the wall 11 outside of the depth of the very fine micropores 12.

What is claimed is:

1. An artificial body of bio-inert membrane-like plastic material, said body having a wall defining a surface and having a plurality of continuous open micropores at least partly communicating with each other and of a maximum linear dimension between 0.1 and 3 microns and a plurality of partitions between said micropores having a maximum width at said surface of not more than 3 microns whereby a continuous layer of epithelial cells can be coated on said surface.

2. An artificial body as set forth in claim 1 wherein said micropores extend in said wall over a depth of between 0.5 and 3 microns.

3. An artificial body as set forth in claim 2 wherein said micropores communicate with each other at least partly within said depth range.

4. An artificial arterial blood vessel comprising a wall defining an interior surface having a plurality of very fine micropores of a maximum linear dimension between 0.1 and 3 microns and a plurality of partitions between said micropores having a maximum width at said interior surface of not more than 3 microns for coating of a continuous layer of epithelial cells thereon.

5. An artificial arterial vessel as set forth in claim 4 having an internal diameter of seven millimeters or less.

6. An artificial arterial vessel as set forth in claim 5 wherein said very fine micropores extend over a depth of between 0.5 and 3 microns.

7. An artificial arterial vessel as set forth in claim 6 which further comprises a reinforcing material in said wall outside of said depth.

8. An artificial vessel comprising a tubular body of bio-inert membrane-like plastic material, said body having a wall defining an interior surface and having a plurality of very fine continuous open micropores of a diameter in the range of from 0.1 to 3 microns and a plurality of partitions between said micropores having a maximum width at said interior surface of not more than 3 microns for coating of a continuous layer of epithelial cells thereon.

9. An artificial vessel as set forth in claim 8 wherein said micropores extend in said wall over a depth of between 0.5 and 3 microns.

10. An artificial vessel as set forth in claim 9 wherein said micropores communicate with each other at least partly within said depth range.

11. An artificial vessel as set forth in claim 8 which further comprises a reinforcing material in said wall outside of said depth.

* * * * *